(12) United States Patent
Buckley et al.

(10) Patent No.: US 7,303,660 B2
(45) Date of Patent: Dec. 4, 2007

(54) ELECTROCHEMICAL TREATMENT OF AN AQUEOUS SOLUTION

(75) Inventors: Alan Buckley, Buckinghamshire (GB); Alexey Yurevich Popov, Moscow (RU); Martin Bellamy, Northamptonshire (GB); Phil Collins, Buckinghamshire (GB)

(73) Assignee: PuriCore International Ltd., London (GB)

( * ) Notice: Subject to any disclaimer, the term of this patent is extended or adjusted under 35 U.S.C. 154(b) by 387 days.

(21) Appl. No.: 10/663,079

(22) Filed: Sep. 16, 2003

(65) Prior Publication Data

US 2004/0060815 A1    Apr. 1, 2004

Related U.S. Application Data

(62) Division of application No. 09/633,665, filed on Aug. 7, 2000, now Pat. No. 6,632,347.

(30) Foreign Application Priority Data

Aug. 6, 1999   (GB) .................................. 9918458.2
Nov. 24, 1999  (GB) .................................. 9927808.7

(51) Int. Cl.
   *C25B 9/00*    (2006.01)
   *C02F 1/461*   (2006.01)
   *C25B 1/26*    (2006.01)

(52) U.S. Cl. ....................... 204/232; 204/260

(58) Field of Classification Search ..................... None
See application file for complete search history.

(56) References Cited

U.S. PATENT DOCUMENTS 3,250,691 A *  5/1966  Broun, Jr. et al. ........... 205/342
3,920,801 A    11/1975 Grotheer
4,432,856 A *  2/1984  Murakami et al. ........... 204/237
4,519,889 A    5/1985  Pellegri et al.
4,586,993 A    5/1986  O'Brien
5,022,974 A    6/1991  Haeivaelae
5,026,946 A *  6/1991  Howard ...................... 585/500
5,135,661 A    8/1992  Patel
5,427,667 A    6/1995  Bakhir et al.
5,445,722 A *  8/1995  Yamaguti et al. ........ 204/228.6
5,616,221 A    4/1997  Aoki et al.
5,628,888 A    5/1997  Bakhir et al.
5,635,040 A    6/1997  Bakhir et al.
5,871,623 A    2/1999  Bakhir et al.
5,932,171 A *  8/1999  Malchesky .................. 205/464
6,217,741 B1 * 4/2001  Doi ........................... 205/620
6,231,747 B1 * 5/2001  Fukuzuka et al. ........... 205/500

FOREIGN PATENT DOCUMENTS

| | | |
|---|---|---|
| DE | 22 12 420 A    | 9/1973 |
| EP | 0 155 479 A2   | 9/1985 |
| EP | 0 612 694 A1   | 8/1994 |
| EP | 0 711 730 A1   | 5/1996 |
| EP | 0 841 305 A2   | 5/1998 |
| GB | 1132281        | 10/1968 |
| GB | 2316090 A      | 2/1998 |
| JP | 53113798       | 10/1978 |
| JP | 07 155764      | 6/1995 |

(Continued)

*Primary Examiner*—Harry D Wilkins, III
(74) *Attorney, Agent, or Firm*—Kenyon & Kenyon LLP (57) ABSTRACT

A method and apparatus are provided for the electrochemical treatment of an aqueous solution in an electrolytic cell. Output solution having a predetermined level of available free chlorine is produced by applying a substantially constant current across the cell between an anode and a cathode while passing a substantially constant throughput of chloride ions through the cell.

25 Claims, 3 Drawing Sheets

FOREIGN PATENT DOCUMENTS

| | | |
|---|---|---|
| JP | 9253650 | 9/1997 |
| JP | 9285789 | 11/1997 |
| WO | WO 92/02462 A1 | 2/1992 |
| WO | WO 98/12144 A1 | 3/1998 |
| WO | WO 98/13304 A1 | 4/1998 |
| WO | WO 98/27013 A1 | 6/1998 |
| WO | WO 98/42625 A1 | 10/1998 |
| WO | WO 99/28238 A1 | 6/1999 |

* cited by examiner

ELECTROCHEMICAL TREATMENT OF AN AQUEOUS SOLUTION

CROSS-REFERENCE TO RELATED APPLICATIONS

This application is a Divisional of U.S. patent application Ser. No. 09/633,665, now U.S. Pat. No. 6,632,347, filed Aug. 7, 2000, and the disclosure of which is incorporated herein by reference.

BACKGROUND OF THE INVENTION

The present invention relates, among other aspects, to a method of operating an electrochemical cell to produce a biocidal solution and apparatus for producing a biocidal solution by way of the electrolytic treatment of an aqueous chloride solution.

In hospitals it is important to provide appropriate levels of sterility, particularly in operating theatres and other situations where invasive treatments are performed. Surgical instruments and other apparatus must be sterilised or disinfected, depending on their application, before use in order to reduce the risk of bacterial infection. One method of sterilisation is the application of heat and pressure in an autoclave. However, this is not suitable for some medical apparatus, such as heat-sensitive endoscopes.

A typical method employed for reprocessing heat sensitive instruments involves the use of chemical biocides, such as glutaraldehyde. This can be unsatisfactory due to improper or incomplete disinfection. Furthermore, exposure to glutaraldehyde fumes can cause asthma and dermatitis in healthcare staff. Also, glutaraldehyde is believed to have relatively low sporicidal activity. Moreover, other disinfectants, such as chlorine dioxide and peracetic acid may suffer from similar handling problems as glutaraldehyde.

For some years, it has been known that electrochemical activation of brine produces a super-oxidised water which is suitable for many applications including general disinfection in medical and veterinary applications and the sterilisation of heat-sensitive endoscopes. There has been a recent interest in the use of super-oxidised water as a disinfectant because of its rapid and highly biocidal activity against a wide range of bacteria, fungi, viruses and spores. Also, super-oxidised water is an extremely effective sterilising cold non-toxic solution which is free from highly toxic chemicals, thereby presenting reduced handling risk.

GB 2253860 describes the electrochemical treatment of water through an electrolytic cell. Co-axially arranged cylindrical and rod electrodes provide anode and cathode (working and auxiliary) flow chambers which are separated by a porous membrane made of a ceramic based on zirconium oxide.

Water is fed from the bottom to the top of the device through the working chamber. Simultaneously, water having a higher mineral content flows through the auxiliary chamber to a gas-separating chamber. An electric current is passed between the cathode and anode through the water in both chambers and the porous membrane separating the chambers. Water flowing through the auxiliary chamber recirculates to the auxiliary chamber by convection and by the shearing forces applied to the water through the rise of bubbles of gas which are generated on the electrode in the auxiliary chamber. The pressure in the working chamber is higher than that in the auxiliary chamber, and gaseous electrolysis products are vented from the gas-separating chamber by way of a gas-relief valve. A change of working mode from cathodic to anodic water treatment is achieved by changing polarity.

This electrolytic process acts on salts and minerals dissolved in the water, such as metal chlorides, sulphates, carbonates and hydrocarbonates. Where the working chamber includes the cathode, the alkalinity of the water may be increased through the generation of highly soluble metal hydroxides. Alternatively, the electrolytic cell may be switched so that the working chamber includes the anode, in which case the acidity of the water is increased through the generation of a number of stable and unstable acids.

A similar electrolytic cell is described in GB 2274113. This cell includes two coaxial electrodes, separated by an ultra-filtration diaphragm (porous membrane) based on zirconium oxide, thereby defining a pair of coaxial chambers. A current source is connected to the electrodes of a plurality of cells via a switching unit to enable polarity alteration of the electrodes to eliminate deposits on the cathode and to connect the cells electrically either in series or parallel.

WO 98/13304 describes the use of such an electrolytic cell in an apparatus to process a liquid, such as water. A liquid is supplied to the cathode chamber only and part of the output from the cathode (catholyte) is recycled to the input of the anode chamber. This input serves as the total supply to the anode chamber. In situations where not all of the solution output from the cathode chamber is recycled to the input of the anode chamber, a proportion of the output from the cathode chamber is drained to waste, this proportion being measured by a flow meter. A constant-voltage DC supply is applied between the anode and the cathode, and the pH and redox potential of the treated solutions are measured and maintained by controlling flow rates through the cell.

A method and apparatus for producing a sterilising solution is described in GB 2316090, the subject matter of which is incorporated herein by reference, wherein a supply of softened water is generated by passing water through an ion-exchange water softener. A saturated salt solution, generated by mixing softened water with salt, is passed through an electrolytic cell to produce a sterilising solution, or used to regenerate the ion-exchange resin in the water softener.

However, all of the systems described above have drawbacks and difficulties. For example, the variable factors, such as the degree of electrolysis in the electrolytic cells, the concentration of dissolved salts and minerals and the flow rates, the fluctuations in electricity supply, ambient temperature and the variability of incoming water supplies present a barrier to ensuring a consistent supply of sterilising or, more correctly, biocidal solution. Thus in order to ensure delivery of a biocidal solution, the electrochemical systems described all rely upon expert intervention to calibrate the cells at the time of installation and to re-calibrate whenever the chemistry of the water supply changes to any significant degree.

As an illustration, the pH of the solution output from the anode chamber (anolyte) may be regulated by adjusting the flow rate of catholyte drained from the cathode chamber. This results in changes to the anolyte flow rate and consequently in changes to the electrochemistry taking place in the electrolytic cell.

Also, the performance of all the above cells and methods is highly dependent on the alkalinity of the water and aqueous salt solutions being treated. In Europe, for example, the alkalinity of potable water can vary from very low (3-15 ppm $CO_3$ as $CaCO_3$) to very high (470 ppm $CO_3$) from one geographical region to another. This means that a cell which is calibrated to produce a biocidal solution of given composition in a first geographical location may not produce the same biocidal solution in a second location, making recalibration necessary. This is a time-consuming and laborious task.

Minimising variation is important to ensure a supply of solution having the required properties, e.g. biocidal activity and pH, especially when thorough sterilisation is required to maintain the health of a population.

Furthermore, it is important to be able to control to a fine degree the final composition of any biocidal solution produced, since the solution must have a high enough concentration of, say, available free chlorine (AFC) to be sufficiently biocidal, but not so high as to corrode or otherwise damage any equipment which is being sterilised. A still further disadvantage of the apparatus described in the prior art is that they are prone to a high level of wastage. Up to half of the initial supply of aqueous salt solution may be discarded after being passed through the cathode chamber. This is especially pertinent where resources such as water are limited or costly.

In the Applicant's experience, none of the above systems is suited to providing a wholly reliable or autonomous supply of biocidal solution. As will be readily appreciated, a "sterilising" solution which does not meet the required level of biocidal efficacy carries a risk of allowing an instrument to spread infection. Moreover, the end user will not be able to detect by visual inspection alone whether the biocidal solution from any one of these systems is within or outside specification.

SUMMARY OF THE INVENTION

Accordingly, the main object of the present invention is to provide a system which delivers for use a biocidal solution only when it has the desired properties, i.e. it is within specification. In this way, the risk of mistakenly using a solution which is not adequately biocidal can be substantially eliminated.

There is also a need to provide a system which not only is capable of producing a biocidal solution in specification but also on demand. Moreover, there is a further need to provide a system which is able to deliver a biocidal solution in specification, on demand, at or close to where the solution is to be used. In addition, there is a need to provide a system which can operate irrespective of the parameters of the local source of input water. Ultimately, the Applicant has set out to achieve a system which is able to deliver biocidal solution in specification, on demand, on site, anywhere.

To this end, and as a result of extensive trials and experiments, the Applicant has devised a system which, by virtue of various innovations, ensures that it will deliver biocidal solutions which are within specification. As will become apparent, the Applicant has also devised a system which is able to produce in specification biocidal solution on demand, on site, anywhere.

From one aspect, the invention resides in a method of operating an electrochemical cell to produce an output solution having a predetermined level of available free chlorine, comprising applying a substantially constant current across the cell between a cathode and an anode and passing a substantially constant throughput of chloride ions through the cell.

In this regard, the Applicant has surprisingly found that by maintaining these two constants, the output solution will have a predetermined level of available free chlorine irrespective of other variables such as local water hardness, alkalinity, pressure etc. In this way, reliance on expert intervention whenever the water supply chemistry changes significantly may be substantially reduced or even eliminated entirely.

Expressed in another way, the present invention resides in a method of electrochemical treatment of an aqueous solution in an electrolytic cell, wherein an output solution having a predetermined level of available free chlorine is produced by applying a substantially constant current across the cell between a cathode and an anode while passing a substantially constant throughput of chloride ions through the cell.

The level of available free chlorine will be set according to the biocidal properties which are required to be imparted to the output solution. The output solution will preferably be required to act as a biocide against a wide range of bacteria, fungi, viruses and spores. An available free chlorine content of about 3 ppm to 300 ppm will generally provide biocidal properties for most envisaged applications. It will however be appreciated that biocidal efficacy is also dependant on pH and therefore that an appropriate balance must be achieved between pH and AFC in order to provide the desired level of bio-compatibility and materials compatibility. For example, the Applicant has found that a level of available free chlorine of approximately 100-250 ppm at a pH of between about 5 and 7 is particularly suitable for the application of reprocessing heat sensitive medical instruments. Other applications, such as its use in non-medical environments, for example as in the processing of poultry and fish and general agricultural and petrochemical uses, the breaking down of bacterial biofilm and water treatment, may demand different levels of available free chlorine.

As will be discussed hereinafter, the Applicant has found that by using a particular cell and flow arrangement, it is possible also to control the pH of the output solution. Where pH control is required, it is preferable that the electrochemical cell comprises two chambers separated by a separator, the first chamber comprising an anode chamber and the second comprising a cathode chamber.

It will be generally understood that the function of a separator in the cell is to isolate the solution in one chamber from the solution in the other chamber while allowing the migration of selected ions between the chambers and the term "separator" as used herein should be construed accordingly. Semi-permeable diaphragms and ion-selective membranes are the most common forms of known separators.

In an electrochemical reaction, it is known that the rate of reaction is generally directly proportional to current within certain limits of the current. Therefore, the current (and thus the rate of oxidation of chloride to chlorine) and flow of chloride through the cell may be set appropriately to produce an output solution having the predetermined level of available free chlorine. The desired current will depend not only on the type of cell being used, for example, the material from which the electrodes are made and the various rare metals used to provide active coatings on the electrodes, but also the size of cell, for example, for a cell having an anode surface area of approximately 100 $cm^2$, an applied current between cathode and anode of 8 Amps is particularly suitable.

In general, the voltage will change as the resistance of the electrolytic cell changes, for example, through deposition of scale in the separator. Accordingly, if the voltage, but not the current, is kept constant, the resistance in the cell will increase as the cell is used. In accordance with Ohms Law, the current will drop and therefore the concentration of available free chlorine in the output solution will fall. This will result in an output solution which may not have sufficient available free chlorine to enable it to act as a biocide.

Therefore, previous systems, such as that described in WO 98/13304, which have relied on a constant voltage across the cell are not always able to produce a predictable level of available free chlorine. In other words, with constant voltage systems, the biocidal properties of the output solution cannot be guaranteed.

However, the Applicant has appreciated that under conditions of constant current, the voltage across the electrolytic cell can be monitored usefully to provide an indicator of other parameters, such as the performance of the apparatus used to carry out the method. For example, as described above, the voltage across the cell will change as the separator becomes plugged with deposits. Also, the voltage will alter as the active coating on the electrodes decreases or a catastrophic event, such as rupture of the separator, occurs in the cell. In this way, monitoring of the voltage provides a means for predicting the longevity of the cell.

In order to achieve a constant chloride ion throughput, it is advantageous to control the flux of chloride ions into the cell. For convenience, the chloride ions are supplied to the cell as a saline solution. Therefore, the throughput of chloride ions through the cell may be determined by controlling salinity and flow rate.

While it is envisaged that the saline solution may be of variable concentration and therefore the flow rate must also be varied to provide a constant chloride feed into the cell, by supplying the saline solution at a substantially constant concentration, only relatively minor changes in flow rate need be made to provide the constant chloride ion throughput.

Desirably, the substantially constant chloride ion throughput is achieved by providing a substantially constant salinity at a substantially constant flow rate. In this way, the quality of the input, in terms of the desired concentration of chloride ions supplied to the cell, is easier to predict and control. A further advantage of aiming to provide a constant salinity is that, should any significant changes in salinity be detected, this may be correctly attributed to an error such as a malfunction of the apparatus or loss of the saline supply. In these circumstances, a failsafe mechanism which is preferably incorporated in the system can operate to prevent output solution which does not meet the desired level of biocidal efficacy, i.e. is out of specification, from being dispensed.

Constant salinity may be achieved by a variety of means, for example by dissolving a known quantity of salt in a known quantity of water. However, this requires a level of skill as well as a knowledge of local water parameters to ensure that the exact amount of salt is added to produce the desired salinity. Accordingly, the Applicant has devised a method of producing a desired salinity which avoids these drawbacks.

In particular, and after much experimentation, the Applicant has found that the chloride input to the cell can be more easily regulated by producing a saline solution from a saturated salt solution, or at least a concentrated salt solution, which is then diluted to the required degree. Preferably, the concentrated salt solution is obtained by adding an excess of salt to water, with further water and/or salt being introduced as required.

More especially, by dispersing discrete volumes of concentrated salt solution into a flow of diluent, the cell can be fed with a substantially constant chloride concentration at a constant rate. The Applicant has found that a saline solution diluted to a concentration of less than 1% w/vol, more preferably in the region of 0.3%, is particularly suitable. The preferred concentration will however be determined according to a number of factors specific to the electrolytic cell being used and the type of output solution desired.

It is preferred if the concentrated salt solution is pulse fed into a flow of diluent water, for example by means such as a peristaltic pump. In this way, each pulse is directed to deliver a known quantity of concentrated salt solution. Accordingly, as the concentrated salt solution becomes more dilute, for example as the supply of salt is depleted, the pulsing rate of the concentrated salt solution into the water flow is increased.

The Applicant has found that benefits are achieved by periodically allowing the concentrated salt solution to become increasingly dilute. By such means, deposits of crystalline salt in the apparatus in which the concentrated salt solution is prepared are reduced.

After the concentrated salt solution has been dispersed in the water, it is further preferred that the salinity is confirmed before entry into the cell, for example, by measuring the conductivity of the saline solution. Advantageously, this is achieved by way of a conductivity probe.

If the conductivity does not fall within the desired range, means for adjusting the salinity to return the conductivity to within the desired range may be provided. This can be achieved by increasing or decreasing the pulse rate to raise or lower the level of concentrated salt solution being fed into the water flow. Alternatively or in addition, means to adjust the flow rate of the water to the cell may be provided. In this way, namely adjustment of the pulses and/or the flow rate, fluctuations in the chloride concentration reaching the cell may be substantially evened out.

Simply pulse feeding discrete volumes of concentrated salt solution into a flow of water diluent can result in a stream of saline solution of variable chloride concentration. For example, the saline concentration may have peaks and troughs along the stream corresponding to the pulses of concentrated salt solution. If the saline solution is not a substantially uniform mix, the conductivity of the solution, if measured prior to entry into the cell, may not be representative of the actual chloride ion content of the saline solution as a whole. Accordingly, it is another object of the invention to provide a means for achieving rapid and effective mixing of the concentrated salt solution in the water diluent.

To this end, the present invention also resides in a method of mixing miscible liquids, comprising dispersing one liquid from a pulsed source into another liquid supplied as a continuous stream, wherein the pulsed liquid is discharged and dispersed in the continuous stream through a plurality of apertures along the flow path to produce a flow of uniformly mixed liquids.

By dispersing a pulsed liquid into another liquid flow through a series of apertures, it is possible to minimise fluctuations in concentration and produce a substantially homogenous mixture.

Expressed in another way, the invention resides in a method of combining at least two liquids, wherein a first liquid is supplied as a continuous stream and a second liquid miscible with the first liquid is supplied from a dispenser into which the second liquid is pulsed and dispersed into the supply stream of the first liquid through a plurality of apertures in the dispenser thereby to produce a continuous homogeneous stream of first and second liquids.

More particularly, the invention comprises a method of combining at least two liquids, wherein a continuous stream of a first liquid is caused to flow through a conduit and a second liquid miscible with the first liquid is pulsed into a liquid dispenser located in the conduit and dispersed into the flow of the first liquid through a plurality of apertures provided in the dispenser thereby to produce a continuous stream comprising a homogeneous mixture of first and second liquids.

Preferably the dispenser is substantially elongate, for example in the form of a length of tube having an external diameter less than the internal diameter of the conduit, which itself may comprise a tube, and has a closed end and an open, feed end. The volume of second liquid which is pulsed into the first liquid will be determined by the volume of the dispenser. Moreover, the length and diameter of the dispenser may be selected to achieve homogeneity of the mixed first and second liquids according to the preferred pulsing rate and pulsed volume of the second liquid.

For maximum effect, the apertures are preferably arranged substantially evenly both longitudinally and circumferentially of the dispenser. Conveniently the apertures comprise perforations and their size may be varied depending on the nature of the first and second liquids involved, for example, in accordance with their viscosities.

By means of the aforementioned mixing method, the Applicant has found that it is able to deliver a fixed volume of concentrated salt solution and simultaneously to disperse the said volume in water to produce a continuous flow of uniformly mixed saline solution. By such means, truly representative conductivity measurements of the saline solution can be made prior to entering the cell.

The final concentration of the mixed saline solution will be determined by the volume of the dispenser, the pulsing rate of concentrated salt solution into the dispenser and the flow rate of the water diluent. For example, the Applicant has calculated that, to produce a 0.3% saline solution from a concentrated salt solution of about 12% w/vol, the dispenser should have a length in excess of about 0.19 m. Ideally, the perforations in the dispenser have an inner diameter of approximately 1 mm, and that about ten perforations are sufficient for this application.

In a typical system practising the method of the invention, the concentrated salt solution is preferably pulsed at a rate of between about 1 to 5 liters per hour and the water diluent is supplied at a rate of between about 150 to 250 liters per hour to achieve the target chloride concentration from the dispenser.

As will be appreciated, the flow rate of the water diluent will be largely determined by the pressure of the supply and may be controlled by its back pressure. Alternatively, or in addition thereto, the water pressure may be regulated by causing the water to flow through one or more flow restrictors, for example, in the form of one or more orifices, provided along the diluent flow path. Ideally, the size of the or each orifice can be increased or decreased to adjust the flow. In this way, the aperture size of the or each orifice may be varied appropriately to regulate the pump output to a constant flow.

Having now achieved the required salinity, for example by the aforementioned mixing method, the actual flow of saline into the cell is then preferably regulated by means of one or more flow regulators before entry into the cell. Ideally, the saline supply is split such that a portion is fed to the chamber including the anode, and the remainder is fed to the chamber including the cathode. Advantageously, the catholyte feed includes its own regulator.

Preferably, a larger proportion of the saline solution is fed to the anode chamber than is fed to the cathode chamber. The Applicant has found that a ratio of at least 80% to 20% fed to the anode and cathode chambers respectively is particularly suitable to produce a biocidal solution from the anolyte. Moreover, in this way, the amount of useful product is maximised whilst the amount of waste is minimised. A particularly preferred feed ratio is 88% saline solution to the anode to 12% to the cathode.

This parallel input to the two chambers of the cell represents a further departure from the prior art which describes the use of series inputs, first to the cathode chamber and then the anode chamber. Such a dual parallel pass allows for even greater control and regulation of the composition of the output solution, thereby substantially ensuring that the final product has the required biocidal properties.

As will be understood, the electrochemical process may be achieved by a plurality of electrolytic cells connected in series electrically, and in parallel hydraulically. Accordingly, references herein to an electrolytic cell should be construed as including a plurality of such cells.

In summary, by applying a constant current across the cell and a constant throughput of chloride ions through the cell as hereinbefore described, it is possible to produce an output solution from the anode chamber which has sufficient available free chlorine to impart biocidal properties to the solution.

Accordingly, the invention may alternatively be expressed as a method of producing a biocidal solution whereby water and aqueous salt solution are mixed to provide a saline solution of constant concentration which is passed through an electrolytic cell at a constant flow rate, and a constant current passed through the saline solution in the cell to produce an output solution having a desired level of available free chlorine.

As previously mentioned, the biocidal efficacy of the output solution, and in particular the anolyte which provides the source of available free chlorine, is strongly dependant on its pH. It is therefore advantageous to tailor the final pH of the anolyte to suit the desired end use. For example, and as described in the Applicant's co-pending United Kingdom patent application no. 9919951.5, a pH of about 5 is suitable for use in treating venous leg ulcers to reduce bacterial infection, while a pH of between 5 and 7 is more suitable for use in the disinfection and sterilisation of heat-sensitive endoscopes. To avoid deterioration of pH-sensitive material, a neutral pH of about 7 may be appropriate. Accordingly, the method of the invention preferably further includes adjusting the pH of the output solution which in turn requires the pH of the anolyte to be monitored.

Altering the pH of the output solution may conveniently be achieved by feeding at least part of the catholyte to the anolyte. The catholyte may be fed to the anolyte either upstream or downstream of the cell. Preferably, at least part of the catholyte is recirculated into the anode chamber. The proportion of catholyte which is fed to the anolyte depends on the final pH required and may be determined by routine investigation. Accordingly, the method of the invention preferably also includes regulating the proportion of catholyte fed to the anolyte.

A further benefit achieved by recycling a proportion of the catholyte is the reduction of the actual amount of catholyte which goes to waste. This is especially desirable as the catholyte waste contains sodium hydroxide. By means of catholyte recirculation, the Applicant has achieved a reduction in waste to less than 10% of the total liquid fed into the cell and even this level of waste can be further substantially reduced. As will be appreciated, cutting the amount of waste liquid to such levels provides a considerable advantage where resources such as water are at a premium. Moreover, by using a by-product of the process to control the pH, the external supply of another process component which may otherwise be required to control pH may be avoided.

Accordingly, and from yet another aspect of the present invention, there is provided a method of electrochemically treating a supply of saline solution in an electrolytic cell having an anode chamber and a cathode chamber separated by a separator, the anode and cathode chambers respectively being provided with an anode and a cathode, and each chamber having input and output lines for the solution being treated, wherein:
  i) saline solution is supplied to the anode and cathode chambers by way of their respective input lines, at least the cathode chamber input line being provided with a flow regulator, and output by way of their respective output lines;
  ii) a substantially constant current is caused to flow between the anode and the cathode; and
  iii) a proportion of the solution output from the cathode chamber is recirculated to an input or output line of the anode chamber by way of a recirculation line.

This and other aspects of the invention are also disclosed in the specification of United Kingdom patent application no. 9918458.2, the subject matter of which is incorporated herein by reference.

It is believed that the output solution owes its biocidal properties to the presence of available free chlorine in the form of oxidising species including hypochlorous acid (HOCl) and sodium hypochlorite ($NaOCl^-$). Such reactive species have a finite life and so, while the pH of the output solution will usually stay constant over time, its biocidal efficacy will decrease with age.

While the output solution will therefore have the desired biocidal efficacy on production, there is a risk that it will fall outside the required specification if stored for any period of time rather than being used immediately. As a further safeguard therefore, the method of the present invention further includes disposing of the output solution after a period of time. In this regard, the Applicant has found that the output solution generally maintains a sufficient level of biocidal efficacy for a period of more than twenty four hours. However, to be certain that the output solution is sufficiently biocidal, the method includes disposing of unused output solution if not used within about twenty four hours of its production.

The Applicant has found that dilution of the output solution produces a bacteria-free water which retains a measure of the biocidal properties of the output solution. Such bacteria-free water has a number of applications including the rinsing of heat-sensitive medical instruments following disinfection or sterilisation and the rinsing of glassware in sterile laboratory or pharmaceutical manufacture applications. New standards are continually being applied to such rinsing agents and the Applicant considers that the properties of the output solution produced in accordance with the present invention, when diluted, provide an effective bacteria-free water (hereinafter referred to as bacteria-free rinse water merely to distinguish it from the neat output solution), which exceeds the required standards. Advantageously, therefore, the method according to the invention further includes the step of diluting the output solution to produce a bacteria-free rinse water.

The Applicant believes that, to ensure the biocidal efficacy of the bacteria-free rinse water, the output solution used to make up the rinse water is preferably not more than about three hours old. In accordance with various failsafe provisions in the preferred method of the invention, any output solution which is detected to fall outside the required specification is generally discharged to waste regardless of its age. However, for the purposes of bacteria-free rinse water, even "in specification" output solution will not be used to generate bacteria-free rinse water if it is more than the desired maximum age.

In order that only the most freshly produced output solution is used to prepare bacteria-free rinse water, it is preferred that output solution emerging from the cell is fed into an intermediate holding location, for example in the form of a first holding means, from which output solution can be drawn for preparation of bacteria-free rinse water. Any output solution which is not used to prepare bacteria-free rinse water is passed into a further holding location, for example in the form of storage means.

For convenience, the output solution may be initially held in the intermediate holding location and from where it is permitted to overflow into the further holding location after a predetermined volume of output solution has been produced. More conveniently, the further holding location may be located beneath the intermediate holding location such that output solution spills directly into it from the intermediate holding location. Ideally, the intermediate holding means comprises a weir tank from which output solution may overflow into a storage tank. To save space and to reduce any risk of external contamination, the weir tank is preferably housed inside the storage tank.

The weir tank provides an ideal location at which to check or confirm that the output solution has the desired parameters. Thus, the weir tank is preferably provided with means to measure redox potential and pH. If the measurement shows that the output solution entering the weir tank falls outside the required specification, the entire contents of the weir tank are preferably diverted to waste thereby avoiding contamination of the second, storage tank and its contents, and avoiding the risk of preparing rinse water from a bad solution. In any event, it is desirable that the contents of the storage tank are disposed of if it contains output solution which has been held for more than about twenty four hours. Furthermore, to ensure that bad output solution entering the weir tank does not accidentally spill over into the storage tank, it is desirable that the flow rate of output solution to waste is faster than its flow rate, or rather its overflow rate, into the storage tank.

The intermediate holding location is preferably open to the atmosphere thereby to reduce the back pressure that may be exerted on the cell and to which the cell is known to be sensitive. In this regard, a weir tank again provides a particularly suitable option.

It is preferable that the intermediate holding means such as the weir tank is of sufficient capacity to meet a typical demand for bacteria-free rinse water from output solution, whilst at the same time minimising the volume which would be wasted should the output solution fall out of specification. As will be understood, the ideal capacity will depend on the desired output of the machine.

A further advantage of using a tank, such as a weir tank, as the intermediate holding means, is that it provides a known capacity into which additional reagents may be added to the output solution contained therein. For example, it is highly desirable to add a corrosion inhibitor to the output solution to prevent corrosion, not only of the apparatus used to generate and dispense output solution, but also the items exposed to biocidal solution during sterilisation and disinfection.

Accordingly, the method according to the invention preferably further includes the step of adding a corrosion inhibitor to the output solution. More preferably, the corrosion inhibitor is added after the output solution has been confirmed to have the desired parameters and prior to dispensing. In this way, corrosion of any apparatus or equipment which is contacted by the output solution is reduced or substantially eliminated.

It is however important that any corrosion inhibitor added to the output solution does not significantly affect the biocidal properties. Moreover, it is also important that the non-toxic, non-hazardous properties of the biocidal solution are not compromised. In this regard, a preferred corrosion inhibitor comprises a combination of a polyphosphate with a molybdate, more preferably a mixture of sodium hexametaphosphate and sodium molybdate.

For convenience, it is desirable to be able to produce output solution on demand, at or close to where the solution is to be used, such as in a hospital. In this way, the need to transport output solution, for example in bottles, to where the solution is to be used may be avoided. In other words, the method of the invention preferably allows for the output solution to be dispensed directly for use.

While the output solution may be dispensed directly for use from the cell if there is an immediate need for the solution, it is also desirable to allow for output solution and, if produced, bacteria-free rinse water to be stored until required. As will be appreciated, the capacity of any such storage means will generally be determined according to the required end use and level of demand. Clearly, these storage means will generally have a greater capacity than the intermediate holding means or weir tank. For example, the Applicant has found that a storage capacity of about 90 liters is sufficient to supply a demand from several typical washer-disinfecter machines which require filling in the shortest possible time. Such washer-disinfecter machines are frequently used for the sterilisation of medical instruments, such as endoscopes. Furthermore, the volume of output solution produced will be determined by the number of electrolytic cells utilised and therefore the capacity of the storage means should ideally be sufficient to cope with this volume. In this regard, it has been found that eight cells connected hydraulically in parallel are together capable of a production volume of approximately 200 liters per hour.

A still further advantage is seen if the volume of output solution and/or bacteria-free rinse water stored is sufficient to facilitate the required dispersion of any additives, such as corrosion inhibitor, to the solutions.

As a further safety mechanism, it is highly desirable for the system producing the output solution to be self-monitoring. In this way, should any parameters, such as process or materials parameters, be detected to fall outside desired values, or any rapid or unexpected changes be detected, the system can be alerted. For example, measurements may indicate that more raw materials are required or that there is a fault in the production process. By incorporating self-monitoring in conjunction with an alert mechanism, the risk of generating a volume of output solution which is out of specification may be substantially reduced.

Advantageously, the system incorporates a self-alert mechanism which is preferably adapted to trigger a self-correction action and/or to notify a user of the system that there is a fault or demand. However, auto-correction, where possible, is preferred before an alarm is raised. For example, self-adjustment of flow rates may be all that is required to cope with fluctuations in local water pressure and alkalinity, whereas a disruption to the supply of input water may not necessarily be susceptible to auto-correction. As a yet further safety precaution or failsafe, it is preferred that production of output solution be stopped should self-correction not be possible or there be no response to an alarm. In this way, the possibility of dispensing output solution which fails to meet the desired parameters can be substantially avoided.

From another aspect, it is desirable if the system allows a user to interact with the production process, such as to obtain information on the performance of the system. Such interaction ideally allows the user to confirm that the production process is functioning properly and, if not, provides the user with guidance as to what action(s) can or should be taken to remedy any faults or deficiencies. Of course, any system faults or deficiencies which are not susceptible to auto-correction are likely to have been brought to a user's attention already by way of an alarm. In circumstances where faults or deficiencies are not easily remedied by the user, or where an indication is provided that the system will require servicing, the user may be prompted to call an expert.

However, it is useful to permit a user to interact with the system other than under alarm conditions, for instance to enable the user to ascertain whether or not there is sufficient output solution and/or bacteria-free rinse water to meet anticipated demand, to advise the user to wait for sufficient output solution to be generated, or to add salt and/or water. In addition, the user may be provided with information as to cell performance and/or its predicted lifespan thereby enabling the cell to be replaced at a convenient time, rather than having to react to a cell failure.

It will be appreciated that the user interface may be governed by computerised means, for example, with provision of suitable firmware and software. Typically, the system may be microprocessor controlled with the interface ideally provided through a display, keypad and/or printer means to provide on-site control.

While it is preferred that the process by which output solution is produced is self-adjusting, in the event that a fault cannot be rectified by self-adjustment, it is advantageous if self-diagnostic means are provided to identify where possible the nature of the fault. Accordingly, it is preferred that the system of the invention further includes a service interface, through which an engineer may gain access to diagnostic information prior to taking remedial action. As with the user interface, the service interface will also be governed by suitable software.

For flexibility and convenience, it is preferred that service interface be accessed either on-site or remotely via a modem or the Internet. An advantage of permitting remote access is that an engineer may check the apparatus on a regular basis without having to travel to the site of the apparatus. This is of considerable benefit when the system has been installed in a far location.

The service interface may also be adapted to provide a history of the production process, for example how the production process has functioned over a period of time and hence to ascertain the remaining life expectancy of a particular component. Also the consumption of output solution can be monitored periodically. Different levels of access to the service interface may be provided, for example access to the production process history may be restricted to engineering personnel.

A further advantage is seen if a system engineer is provided with means to alter operating parameters remotely where possible, thus reducing the necessity for the engineer to attend the system if the process requires only minor adjustment. Also, this enables the engineer to monitor the system to keep it working smoothly. Indeed, by facilitating remote access, it is possible for an engineer to make adjustments to the system well before any alert mechanism is triggered. In such a way, intervention by the user can be kept to a minimum. Indeed, under typical conditions, a user may be required only to feed the system with salt at appropriate intervals, as any other controls or adjustments are made by the system itself or remotely through the service interface.

If remote access is provided via the Internet, for example, it is envisaged that such access may also include means by which the system can alert an engineer of a problem, for example, by e-mail, so that the apparatus may be attended to before a potentially more serious fault occurs. It is also possible to alert an engineer by fax, short message service (SMS) or other such means. All of these service interface features can help to reduce downtime of the apparatus and facilitate siting of apparatus in diverse locations.

All of the aforementioned features contribute to providing a system which delivers, for use, an output solution which has sufficient available free chlorine to impart biocidal properties to the solution. In other words, and by means of the various self-checking and alert mechanisms, it will be appreciated that the system is adapted to prevent output solution which is not within specification from being dispensed.

From another aspect, the present invention resides in apparatus for producing an output solution having a predetermined level of available free chlorine comprising an electrolytic cell, means for passing a saline solution having a substantially constant chloride ion concentration through the cell, means for applying a substantially constant current across the cell and means for dispensing output solution from the cell.

As will be appreciated, by means of such apparatus, it is possible to produce an output solution having biocidal properties almost anywhere where there is a supply of process water, salt and electricity.

Preferably, the apparatus is provided with water input means including a supply tank for storing and dispensing process water. Since pressure from a local water source may vary, such a supply tank compensates for any fluctuations and thereby acts as a hydraulic capacitor. Conveniently, the supply tank is of sufficient capacity to cope with any such fluctuations. A further advantage of storing process water is that the supply tank provides a 'reserve' supply of water to the process, should the local supply be disrupted for any reason.

The means for generating saline solution having a substantially constant chloride concentration preferably comprises salt input means, water input means, means for dissolving salt in water to produce a concentrated salt solution, means for mixing and diluting the concentrated salt solution to a desired concentration and means for feeding the resulting saline solution to the electrolytic cell at a regulated rate.

It is preferred that the salt input means comprises a chute which ideally holds a known quantity when filled to a predetermined level and which transfers salt to a concentrated salt solution make-up tank. For example, the Applicant has found that about 6 kg of salt is convenient because this corresponds to an easily-handled amount and, under typical operating conditions, provides an adequate supply of salt to the apparatus for a period of, say, two days.

Salt is generally dissolved in water from the input means to produce a concentrated salt solution in the make-up tank. Following an input of fresh salt, the solution may at least initially be a saturated salt solution. A level detector may be provided in the make-up tank to provide an indication when the salt level is insufficient to produce a concentrated saturated solution. Such a detector is preferably linked to an alert mechanism, such as a visual or audible alarm, which is activated to advise a user that more salt is required. Moreover, the apparatus is preferably provided with a mechanism designed to halt production of output solution if the alarm is not responded to within a specified time period.

The concentrated salt solution is diluted with process water to the desired concentration. As previously described, this is preferably achieved by pulse feeding concentrated salt solution, for example using a peristaltic pump, from the make-up tank into a flow of process water supplied by the supply tank via a dispenser. The dispenser may be provided with a series of apertures thereby ensuring that the pulses of concentrated salt solution are substantially evenly dispersed in the process water. By these means, a saline solution of a desired concentration may be produced.

Moreover, to confirm the concentration of chloride ions in the resulting saline solution, a conductivity probe or any other suitable measuring means is conveniently provided before the solution enters the cell. If the chloride ion concentration as measured does not fall within the desired range, the pumping rate of the saturated salt solution and/or the process water may be adjusted by feedback means from the conductivity probe. Additionally, one or more flow regulators may be provided as a fine tuning mechanism for the saline solution entering the cell.

Having confirmed the conductivity and regulated the flow accordingly, the saline solution is fed into an electrolytic cell. Electrolytic cells for producing biocidal solutions are of course known and preferably comprise co-axial cylindrical and rod electrodes separated by a separator, such as a semi-permeable or ion-selective membrane. Usually the electrodes are made of titanium, and the anode is provided with an active metal oxide coating. Generally, the cylindrical electrode is connected to the positive output of a current source, and the rod electrode is connected to the negative output, but a reversal of this arrangement is also known.

While such known cells may be used in the system according to the present invention, the Applicant has developed a new cell which is particularly suitable. From another aspect therefore, the present invention comprises an electrolytic cell having an anode chamber and a cathode chamber separated by a separator, the anode and cathode chambers respectively being provided with an anode and a cathode, each chamber having at least one input and output, wherein the separator is in the form of a semi-permeable membrane comprising an aluminium oxide based ceramic containing zirconium oxide and yttrium oxide.

As will be understood, it is a desired function of the separator that it be sufficiently permeable to permit an adequate flow of solution between the two chambers to give an acceptable electrical resistance while being sufficiently non-permeable to prevent gross mixing of the anolyte and catholyte solutions. In this regard, the Applicant has found that a ceramic comprising up to 20% zirconium oxide and up to 2% yttrium oxide satisfies this function. More desirably, the ceramic consists essentially of 80% aluminium oxide, 18.5% zirconium oxide and 1.5% yttrium oxide. The porosity of the ceramic is preferably within the range of 50-70% and the pore size between 0.3-0.5 microns. Furthermore, the ceramic preferably has a wall thickness of 0.3-1.0 mm.

A particularly suitable ceramic membrane composition and its method of manufacture is disclosed in the specification of the Applicant's own co-pending United Kingdom patent application no. 9914396.8, the contents of which are herein incorporated by reference.

Alternative separation means may be provided by an ion-selective membrane comprising a perfluorinated hydrocarbon containing sulfonate ionic groups having channels which permit the passage of cations only through the membrane, for example, the membranes sold by DuPont under the trade mark Nafion®.

As with the known cells referred to, the electrolytic cell advantageously comprises co-axially arranged cylindrical and rod electrodes, preferably with the cylindrical electrode forming the anode and the rod electrode forming the cathode. Preferably, the cathode has a uniform cross-section along its effective length.

Moreover, the anode is preferably formed from titanium, and desirably includes an electrocatalytic (active) coating for the oxidation of chloride ions, for example mixtures of any or all of ruthenium oxide, iridium oxide, and titanium oxide.

The electrolytic cell may alternatively be of a filter-press type design, with flat electrodes separated by an ion-selective membrane, such as that previously referred to and sold under the trade mark Nafion®. However, such a cell is less preferred than the cylindrical and rod electrode type.

As previously described, the electrolytic cell preferably includes separated anode and cathode chambers, and saline solution is fed into both chambers simultaneously with a constant current applied between the electrodes. Output solution is passed from the anode chamber to dispensing means while the catholyte is either directed to waste or a portion thereof recirculated into the anode chamber.

The dispensing means preferably comprises one or more storage tanks. However, in view of the desirability to use only the output solution which has been produced within a preferred time period, as described above, the Applicant has devised an arrangement of storage tanks which allows for this. Accordingly, the output solution is preferably fed into an intermediate holding tank, such as a weir tank, before it is transferred to one or more main storage tanks.

In order to confirm that output solution entering the intermediate tank has the desired characteristics, quality control means such as redox and pH probes may be incorporated to provide data on the output solution as it enters the tank. The intermediate tank may be further provided with discharge means to divert output solution, which does not fall within the specification, to waste. Other means may also be provided to feed in-specification output solution from the intermediate tank to a storage tank from which the solution may be dispensed for use and/or dispensed to a yet further storage tank where it may be diluted to produce bacteria-free rinse water.

When charged to a predetermined level and having had its redox potential and pH confirmed as falling within specification, the weir tank allows output solution to overflow into the main storage tank.

As will be appreciated, gases such as hydrogen and chlorine are generated by the electrochemical reaction in the cell. Since these gases are potentially dangerous and the chlorine itself malodorous, it is highly desirable that these gases be removed from the output solution before it is dispensed for use. Preferably, the gases are vented from the output solution through one or more filters. Ideally, a filter, such as a carbon filter, is located to catch such gases from the output solution in the weir and/or other storage tanks, such as the bacteria-free rinse water storage tank.

For most applications, the apparatus as described is preferably housed in a self-contained unit. However, it may alternatively be provided in a modular format, for example so that it may be constructed on site within the restrictions of the available space. For ease of assembly and maintenance, and whether a self-contained or modular format, connections between the components of the apparatus are most conveniently provided in the form of rigid pipes. The pipes may be connected to the components and/or each other by means of universal joints or threaded connections. Accordingly, when one or other of the components is replaced or removed for maintenance, the need to use tools such as spanners may be substantially avoided.

In assembling the individual components to form the apparatus, the Applicant has done far more than simply arranging the components in such a way as to accommodate them in a convenient housing. In particular, the Applicant has expended much time and effort to achieve an assembly which provides both practical and technical benefits. For example, the Applicant has arranged the components so that the various pumps are located at a low level within the apparatus thereby not only lending stability to the apparatus but also helping reduce vibration of the apparatus caused by operation of the pumps. Similarly, location of the process water supply tanks and the concentrated salt solution make-up tank at a low level provides further stability. Low level location of the saturated salt solution make-up tank is also particularly convenient as it provides for feeding from the salt chute at a comfortable height.

Furthermore, it has been found that by locating the electrolytic cell at a level which is higher than the aforementioned input tanks, back pressure on the cell is substantially avoided. Moreover, since the electrolytic cell is at a relatively high level, this makes it possible for output solution to be transferred to one or more storage tanks also at a high level. In this way, dispensing of the output solution from the or each storage tank, either as neat biocidal solution or as bacteria-free rinse water can be achieved by gravitational feed. However, where it is required to dispense a large volume of solution over a short period of time, for example, as required to fill a washer-disinfecter machine, gravitational feed alone may not be sufficient and so it is advantageous if the output lines also include pumping means.

As will be appreciated, it is highly desirable for the carbon filter to be located at a high level with respect to the apparatus. In this way, it is possible to maximise the collection of gases generated by the electrochemical reaction and to minimise the risk of exposing personnel to those gases.

Means to detect any leakage of liquids from the apparatus may also be included, such detection means advantageously being in communication with the user and or service interface so that remedial action may be promptly taken. Ideally, the user/service interface will provide information as to the source of the leak. Leak detection means may be conveniently located in a drip tray positioned at the base of the apparatus.

In order that the system is not compromised through lack of cleanliness in the apparatus, it is desirable that it be self-cleaning, preferably by means of an automatic self-cleaning cycle. In this respect, it is advantageous if the self-cleaning cycle is designed to ensure that at least those parts of the apparatus which may come in contact with output solution are cleaned. Effectively, this means that various pipes, valves, pumps, probes, connectors and storage tanks are required to be cleaned. Since the apparatus is adapted to generate an output solution having biocidal properties, this solution is ideal to carry out the cleaning. In this way, the apparatus is also disinfected and sterilised.

Accordingly, the method of the invention further includes an automatic self-cleaning step whereby output solution is periodically passed through substantially the entire apparatus. As will be appreciated, because the system operates in such a way as to prevent output solution which is not within specification from being dispensed, only output solution which has the required biocidal properties may be used in the cleaning step.

To ensure that all surfaces of the storage tanks are contacted by the output solution during the cleaning process, it is advantageous if the solution is introduced into each tanks by way of a spray bar.

In addition, to minimise downtime of the system, it is preferred that the operation of the self-cleaning cycle takes place at a time when the solution is least likely to be demanded, for example, at night.

It is a preferred object of the invention that the system can operate irrespective of local conditions. Since the nature of water supplies may vary enormously between locations, for example its supply pressure and temperature, hardness, pH and microbial count, it is desired to provide a system which can be adjusted to perform irrespective of these parameters. Accordingly, it is advantageous if the apparatus includes means to compensate for parameters which fall outside the preferred operating range.

For example, variations in water supply pressure can be compensated for by means of the process water supply tank. A high microbial count can be reduced by suitable filtration before the water is allowed to enter the supply tanks, this is especially pertinent to use of apparatus in developing countries where the water may be of poorer quality.

Variations in pH of the supply water may be compensated for by adjusting the pH of the output solution to the required level by recirculating a proportion of the catholyte from the cathode chamber of the cell into the anode chamber. This pH adjustment process and its advantages have been described above.

Water hardness may also affect the system, resulting in deposition of magnesium and calcium ions not only in the supply tanks, but more seriously, in the cell itself. Such deposition may cause plugging of the separator which increases the cell resistance and this in turn increases the wear on the cell. Life-expectancy and cell efficiency are thereby reduced. Also, the use of unsoftened water can make it more difficult to control the pH of the anolyte. Accordingly, it is preferred to incorporate means for substantially removing the hardness ions from the water supply or at least reducing the amount of such ions before it passes into the supply tanks. Such means maybe by way of a suitable water softener, for example one containing a cation-exchange resin.

By virtue of the aforementioned features, the Applicant has devised a new system for generating an extremely effective non-toxic, biocidal solution which acts against a wide variety of bacteria, fungi, viruses and spores and is suitable for many applications including disinfection and cold sterilisation. In addition, the system can be operated and maintained regardless of location and requires only water, electricity and salt to be put into effect. The system can be operated either continuously or in response to demand and can be adjusted to produce a solution tailored for a particular end use. Moreover, because of the various failsafe means it incorporates, it is virtually impossible for an end user to be provided with a biocidal solution of inadequate efficacy.

In summary, the Applicant has invented a system which is not only adapted always to deliver biocidal solution which falls within the desired specification, but also to deliver such solution on demand, on site, anywhere.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
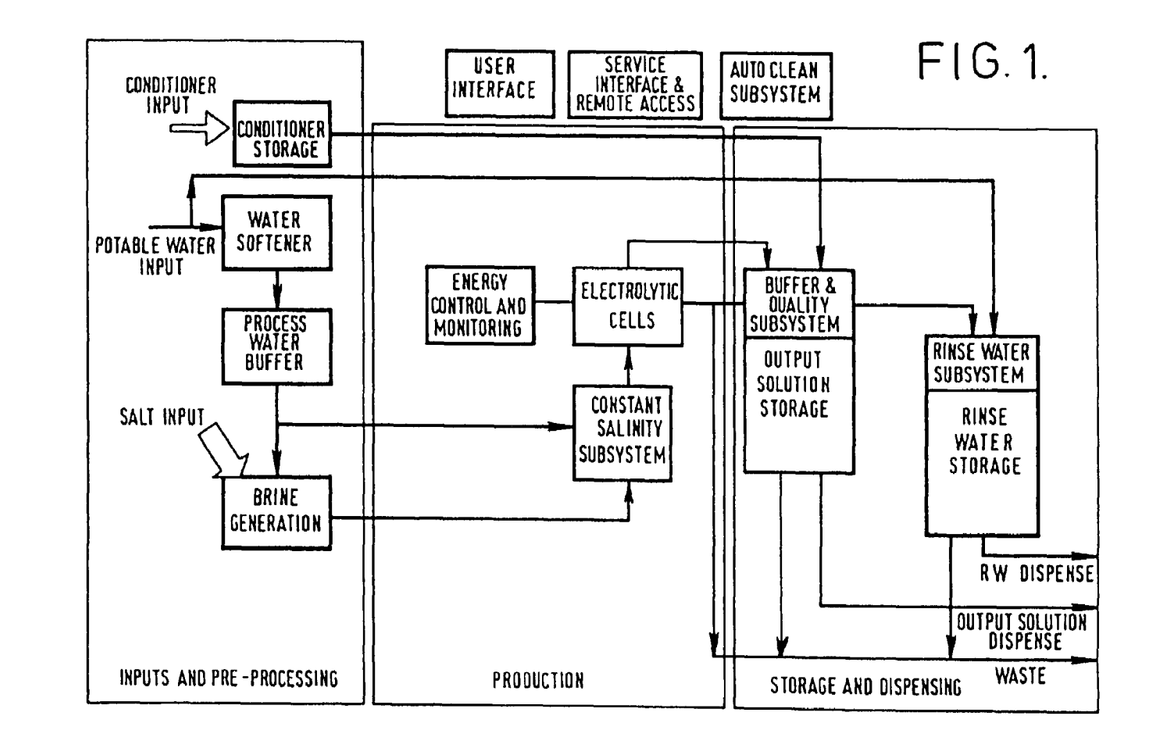
FIG. 1 shows an embodiment of the invention in schematic outline.

Referring first to FIG. 1, the schematic outline of the invention is broken down into three main processing stages, namely an inputs and pre-processing stage, a production stage and a storage and dispensing stage. While referred to as stages, it will of course be appreciated that the process of the invention may be carried out continuously.

In the first (inputs and pre-processing) stage, there is an input of potable water which, for the purpose of generating saline solution for use in the electrolytic cell, is first passed through a water softener zone where excessive magnesium and calcium ions are removed. The softened water is then passed into a process water buffer zone where it is held until required for use in the production of brine. Potable water input is also passed directly to the storage and dispensing stage for use in the preparation of bacteria-free rinse water, but for this purpose there is no need for the water to be softened prior to use.

The first stage also includes a salt (NaCl) input, usually of vacuum dried crystalline salt which is commercially produced to a consistent standard, to a brine generation zone where a concentrated salt solution is made up from the salt and the softened water obtained via the process water buffer zone.

A further input is provided for additional agents, such as a corrosion inhibitor, used to condition output solution produced by the process. The conditioner is passed to a conditioner storage zone where it is held until required.

Turning to the second (production) stage, this comprises a constant salinity subsystem in which a saline solution of substantially constant concentration is produced by dilution of the brine from the brine generation zone with softened water from the process water buffer zone to the desired concentration. The resulting saline solution is passed from the constant salinity subsystem to one or more electrolytic cells, each including cathode and anode chambers (not shown), and across which a substantially constant electric current is applied. The applied electric current is maintained constant via an energy control and monitoring zone.

Catholyte and anolyte are produced from the cathode and anode chambers respectively as a result of the electrochemical treatment of the saline solution in the cells. Anolyte and a portion of catholyte which is not recirculated to the anode chamber are both dealt with in the third (storage and dispensing) stage. In particular, catholyte which is not recirculated is directed to waste and anolyte, otherwise referred to as output solution, is passed to a buffer and quality subsystem. The output solution is tested in the buffer and quality subsystem and, if it fails to meet the quality standards, it is also directed to waste. If the output solution falls within specification, a quantity of conditioner, such as a corrosion inhibitor, is added to it in the buffer subsystem and the output solution is then permitted to pass either into an output solution storage zone from where it is subsequently dispensed for use or into a rinse water subsystem.

Output solution directed to the rinse water subsystem is diluted with potable water from the potable water input and is then passed to a rinse water storage zone from where it is subsequently dispensed.

Provision is also made for discharging output solution from the output solution storage zone and rinse water from the rinse water storage zone to waste.

Information on the various processing stages and the ability to interact with the process is provided by means of a user interface and a service interface. The service interface also provides for remote access to the process, enabling an off-site engineer to obtain information on and make adjustments to the processing in each of the three stages.

There is also provided an autoclean subsystem to permit cleaning of the system, either at regular intervals or whenever convenient.

Figure 2:
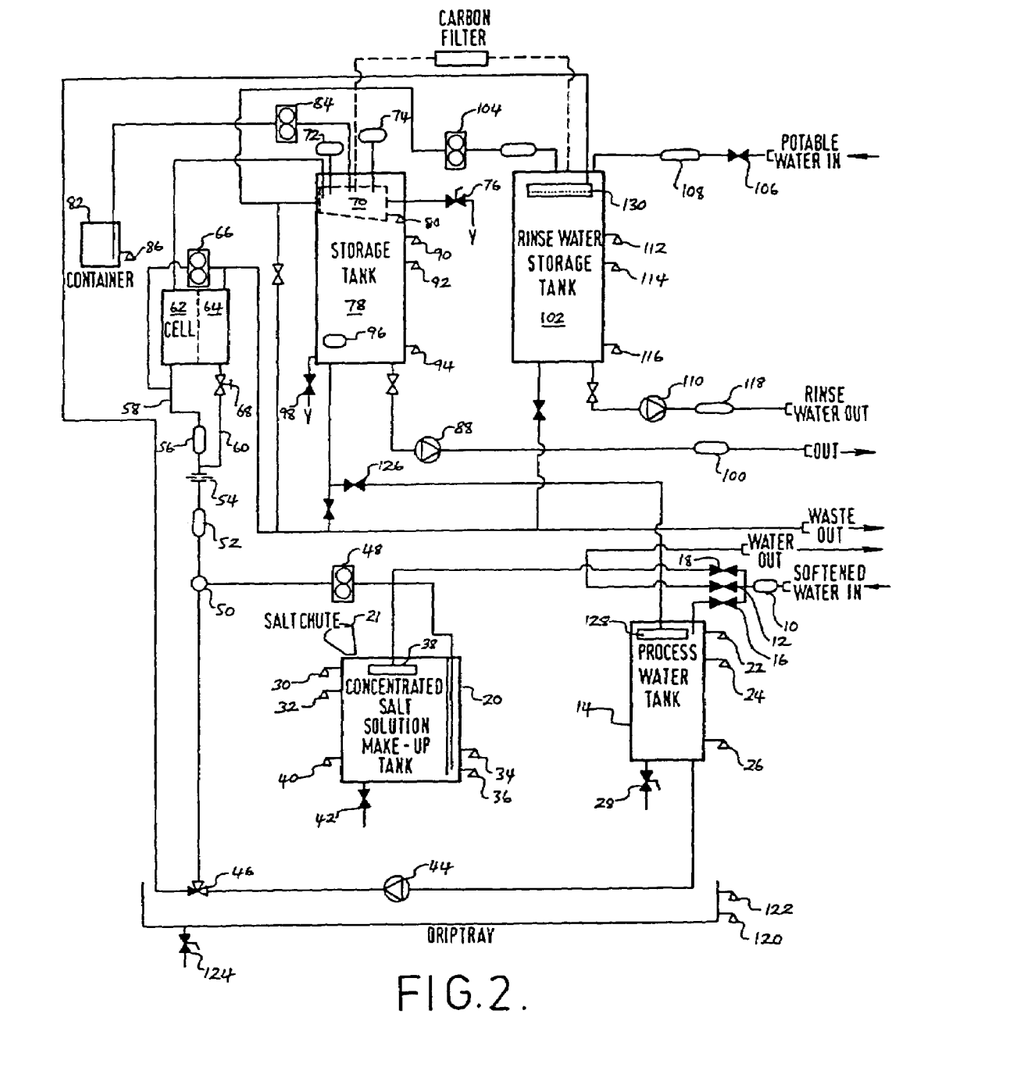
FIG. 2 is a detailed flow diagram of the invention as outlined in FIG. 1.

FIG. 2 is a flow diagram or "hydraulic map" showing in more detail the invention already outlined in FIG. 1. Potable water is passed through an external water softener containing a cation exchange resin (not shown) thereby exchanging hardness ions of calcium and magnesium onto the resin and releasing sodium ions into the water.

Incoming softened process water is monitored by a sensor 10. The sensor 10 ascertains whether the incoming water is at a temperature within the range under which the process can reasonably operate, namely between about 5 and 35° C. Other parameters such as the incoming water's pressure, softness, alkalinity, pH, conductivity and microbial count can also be monitored by the sensor 10 to establish that it falls within acceptable levels for the process.

If the sensor 10 detects that the properties of the incoming softened process water do not fall within acceptable limits required by the specification, the water is diverted through a waste discharge manifold (not shown) to a drain via valve 12. On the other hand, if the incoming softened process water is in specification, it is allowed to flow into internal process water tank 14 through inlet valve 16 or is diverted via inlet valve 18 to the concentrated salt make-up tank 20.

Buffer storage for the process water in the event of a temporary interruption in the water supply is provided by the process water tank 14 having a large enough volume. Moreover, the tank 14 also has sufficient capacity in order to eliminate pressure fluctuations in the fluid supply to the electrolytic cells.

The process water tank 14 includes a plurality of level detectors for monitoring and controlling the process water level in it. Level detector 22 is a safety device which is activated only when the process water in the tank reaches a predetermined extra high level to stop the charging of the tank with process water and raise an alarm. Another level detector 24 is activated when the level of liquid in the tank reaches a predetermined high level to stop further inlet water from entering the tank 14 by closing a valve 16. Water will begin to re-charge the tank 14 after a predetermined time has elapsed below the high level. Level detector 26 is activated when the process water in the tank 14 reaches a low level to prevent production of output solution. The tank 14 also includes a valve 28 which allows liquid to be drained. Furthermore, the tank 14 is designed to comply with local regulations, such as the class A air break requirements as required in the United Kingdom by Building Regulations Bylaw 11.

Concentrated salt solution is made-up and stored in a concentrated salt solution make-up tank 20. To make up the concentrated salt solution, vacuum dried crystalline salt (BS998:1990) is added to the tank 20 via a salt chute 21 having a capacity which is able not only to accommodate a typical salt input of about 6 kg, but to tolerate an amount of overfilling sufficient to keep the system supplied for approximately 1 to 2 days at a normal operation level.

To monitor liquid levels within the concentrated salt solution make-up tank 20, level detectors are also provided. Thus, level detector 30 is a safety device which is activated by an extra high level of liquid in the tank 20 and acts to close a valve 18 to prevent overfilling of the tank 20 and to raise an alarm, but will not halt production of output solution. A level detector 32 is activated by a high level of liquid in the tank 20 to stop further water filling the tank 20 by closing the valve 18. A level detector 34 is activated by a low level of liquid in the tank 20 and operates to open the valve 18 to charge the tank 20 with softened water. A low level detector 36 is activated by a very low level of liquid in the tank 20 to halt production of output solution and to raise an alarm.

Softened water is fed through the valve 18 and automatically fills the tank 20 through a spray-bar 38 until the high level switch 32 is activated. Salt in the tank 20 dissolves in the water to produce a concentrated salt solution with the level of salt reducing as more salt is dissolved.

A further level detector 40, this time for the salt, is located towards the bottom of the tank 20. The salt level detector 40 is activated when the amount of salt in the tank 20 is depleted such that it is approaching a level insufficient to produce a concentrated salt solution. On activation, an alarm is raised which alerts an operator that more salt is required. The request to add salt is displayed on the user interface (FIG. 1) and replenishment of the salt supply in the tank 20 may be carried out manually by an operator or automatically through a control system. The user interface is operative to display a suitable message when sufficient salt has been added.

Finally, the tank 20 also includes a manual drain valve.

Concentrated salt solution from the salt make-up tank 20 is diluted with process water from the process water tank 14 to produce a saline solution of substantially constant chloride ion concentration. In more detail, process water is continuously pumped by process water pump 44 through a valve 46 towards an electrolytic cell pack and concentrated salt solution is pulse fed into the flow of process water via an adjustable speed peristaltic pump 48. The pulses of concentrated salt solution are dispersed into the substantially continuous stream of process water through a perforated tube 50 thereby evening out the pulses to produce a flow of saline solution of uniform concentration.

The flow rate of the resulting saline solution as it flows towards the cell pack is monitored by a flow meter 52 and if necessary is modulated by a flow regulator in the form of an orifice plate 54. The flow rate is changed simply by changing the size of the orifice in the plate. Different orifice plates may be chosen to suit site conditions.

Prior to entering the cell pack, the concentration of chloride ions in the saline solution is checked by means of a conductivity sensor 56. If the conductivity measurement indicates that the chloride ion concentration has fallen below the desired level or has risen above it, the pulsing rate of the peristaltic pump 48 is increased or decreased respectively to alter the amount of chloride ions being dispersed into the process water through the perforated tube 50 thereby compensating for the fall or rise in chloride ion concentration.

The size of the aperture in the orifice plate 54 is also adjusted to regulate the flow of chloride ions into the cell pack. Adjustment of the pulsing rate and the flow rate together provide a fine tuning means to ensure that the cell pack is supplied with a constant chloride ion throughput.

On the other hand, if the conductivity of the saline solution as measured by the conductivity sensor 56 falls outside a predetermined range such that it is not possible to adjust the pulsing rate and/or flow rate to bring the conductivity within the required range, and hence make it virtually impossible for the cell pack to produce output solution having the desired level of available free chlorine, an alarm is raised and the flow of saline solution to the cells is ceased pending rectification of the problem.

If the saline solution already provides or can be adjusted to provide the requisite throughput of chloride ions, it is split into two streams 58, 60 before being fed through the cell pack. Typically the cell pack consists of eight electrochemical cells, with two sets of four cells connected hydraulically in parallel. For simplicity, only one cell is illustrated. However, the number of cells in the cell pack is determined by the output volume required from the particular system. Each cell has an anode chamber 62 and a cathode chamber 64 and the flow of saline solution is split such that the greater portion is fed to the anode chamber 62 and the lesser portion is fed to the cathode chamber 64. In this embodiment, approximately 90% of the saline solution is passed through the anode chamber(s) with the remainder passed through the cathode chamber(s). The flow rate of saline solution through the cathode chamber is much lower than for the anode chamber and the pressure in the cathode chamber is also lower.

As the saline solution flows through the electrolytic cells, a fixed current of between 7-9 amps (typically 8 A) is applied to each cell causing electrolysis of the saline solution thereby generating available free chlorine in the resulting anolyte, elsewhere generally referred to as the output solution. In order to produce output solution at a relatively neutral pH, namely between 5 and 7, the pH of the output solution is at least partially controlled by dosing a portion of the catholyte to the inlet stream 58 for the anode chambers 62. The catholyte is dosed to the inlet stream 58 by an adjustable peristaltic pump 66 and the dosing rate is increased or decreased to achieve the target pH. In this way, the system is also adapted to cope with varying alkalinity of the input potable water. The remaining catholyte which is not dosed into the input stream 58 for the anode chambers 62 is directed to waste, if necessary diluting it prior to disposal.

Since the flow rate of the saline solution into the cathode chamber 64 also has an influence on the pH of the output solution, a flow regulator 68 is provided to control the flow of saline entering the chamber. The flow regulator 68 can be manually adjusted if there is a variation in input water quality. Output solution is fed from the outlet of the anode chambers 62 of the cell pack into an intermediate weir tank 70.

The pH and redox potential of the output solution in the weir tank 70 are measured by a pH meter 72 and a redox probe 74 respectively. If the pH and redox potential do not fall within the desired parameters, a valve 76 is opened and the contents of the weir tank 70 are drained to waste. The contents of the tank 70 are drained to waste in any event if they have remained in the tank for about three hours. The pH meter 72 is linked to pump 66 to adjust the level of catholyte dosed to the anode chambers 62 thereby enabling the pH of the output solution to be adjusted to bring the output solution within the desired pH range. If the pH and redox potential of the output solution are determined to fall within the desired parameters, confirming that the output solution has the necessary biocidal efficacy, the valve 76 is kept closed and the output solution is allowed to fill the weir tank 70 until it reaches a level where it floods over into a storage tank 78. The weir tank 70 includes a level detector 80 for monitoring when the level of output solution in the tank falls to a predetermined low level. When the low level detector 80 is activated, the production of sterile rinse water is stopped.

Provided the pH meter 72 and the redox probe 74 confirm that the output solution has the desired parameters, a corrosion inhibitor, such as a mixture of sodium hexametaphosphate and sodium molybdate, is dosed as a solution from a storage container 82 into the output solution in the weir tank 70 by a peristaltic pump 84. A sensor 86 is mounted in the storage container to monitor low levels of inhibitor and trigger an alert mechanism which alerts the system that there is a need for inhibitor to be supplied to the storage container 82.

In specification output solution spills from the weir tank 70 into the storage tank 78 where it remains until a demand for it is received. For example, when it is required for a cycle of a washer-disinfecter machine, the system receives a demand signal from a washing machine interface control module triggering operation of a dispensing pump 88. Typically, the dispensing pump 88 is rated so that it can supply output solution to three washing machine vessels of 25 liter capacity in 180 seconds (1500 liters per hour, 3 bar line pressure). The capacity of the storage tank 78 is therefore such that it too can fulfil the volume requirement.

The storage tank 78 includes various level detectors for monitoring liquid levels in the tank. A level detector 90 is activated by an extra high level of output solution within the tank, raising an alarm and stopping production. A level detector 92 is activated before the detector 90 as the volume of output solution rises in the storage tank 78 and simply stops production. As the output solution is dispensed and after a period of time below the level of detector 92, production of output solution is recommenced. A low level detector 94 is activated when the level of the output solution falls to a low level, raising an alarm and preventing further dispensing to the machine.

A pH probe 96 for monitoring the pH of the output solution is provided within the storage tank 78 so that if the pH of the output solution drops out of specification, it is routed to waste by a valve 98 located on the outlet of the storage tank 78. In addition, if the output solution has been stored for 24 hours, it is similarly routed to waste. In this way, output solution which is out of specification is never dispensed. In order to monitor the flowrate and amount of output solution dispensed from the storage tank 78, a flow meter 100 is linked to 'no flow' and leak detection routines within a user/service interface to alert the system, for example, that the discharge valve 98 is closed during a requested discharge, or that an unrequested discharge is occurring.

Since the output solution held in the weir tank 70 is never more than three hours old, it is used to produce bacteria-free rinse water. Fresh output solution is dosed at a predetermined rate from the weir tank 70 to a rinse water storage tank 102 via a peristaltic pump 104. Filtered potable water flows into the tank 102 through a valve 106 where it mixed with and dilutes the output solution to a concentration of about 2%. If the local water supply is of poor quality, a higher concentration of output solution in the rinse water, for example a 5% solution, is preferred. Accordingly, the dosing rate of pump 104 is determined by the incoming potable water supply and is monitored by a flowmeter 108. Both potable water and output solution are added to the rinse water storage tank 102 simultaneously and a minimum standing time of two minutes is always allowed before dispensing the resulting mix. This ensures sufficient contact time for the output solution to diffuse in and activate the potable water. Rinse water is stored in the rinse water storage tank 102 until it is required by, for example, an endoscope washing machine. A dispensing pump 110 is activated on receipt of a demand signal from a washing machine interface control module. As with the dispensing pump 88, the dispensing pump 110 is similarly rated to meet the demand of filling three washing machine vessels of 25 liters capacity in 180 seconds (1500 liters per hour, 3 bar line pressure) and the capacity of the rinse water storage tank 102 is also dictated by this typical demand scenario.

The rinse water tank 102 is provided with a plurality of level detectors to monitor levels of rinse water. A level detector 112 is activated when there is an extra high level of rinse water the tank 102, alerting the system and stopping any further production of rinse water. Another level detector 114 monitors high rinse water level in the tank 102 and when activated stops rinse water production. After a predetermined period of time has elapsed and when the rinse water level has fallen, the high rinse water level detector 114 is deactivated and the production of rinse water is recommenced. When there is only a low level of rinse water in the tank 102, a level detector 116 is activated raising an alarm and preventing further rinse water from being dispensed.

The flowrate and total rinse water dispensed is monitored by a flowmeter 118, which also is used in 'no flow' and leak detection routines linked to the user/service interface (FIG. 1). By automatic monitoring of liquid levels in the weir tank 70, the storage tank 78 and the rinse water tank 102, and by discharging the output solution and rinse water periodically, the system is able to self-adjust to allow it to meet demand at all times. Gases generated by the electrolytic reaction in the cell pack, mainly hydrogen and chlorine, are vented through a carbon filter located above the weir tank 70 and rinse water tank 102 to reduce the quantity of chlorine which escapes.

The system also includes a drip-tray provided with leak detection means in communication with the user/service interface (FIG. 1). The drip tray is a shallow vessel housing two level detectors 120, 122, one being a low level detector and the other an extra high level detector. The low level indicator 120 is activated by any small leak within the machine and activates an alarm when the liquid level rises above the detector, but does not halt the production process in any way. However, the extra high level detector 122 activates an alarm and halts the production and dispensing of output solution. A manual valve 124 is provided at the base of the drip tray to allow drainage of the tray.

To maintain the system properly, it is necessary to sterilise the storage tanks and discharge lines on a regular, typically daily, basis. Output solution having the desired biocidal properties as confirmed by its measured parameters and age is flushed through the filters, tanks and pipework to eliminate bacterial growth in these areas. In particular, before the cleaning cycle is commenced, the output solution tank 78 is replenished to a high level as detected by the detector 92 ensuring that sufficient output solution is available for the cycle, and the pH and redox potential of the output water are confirmed as being within specification by the pH probe 72 and the redox probe 74. The pH and redox potential will change during the cleaning process and need not be monitored once the cleaning process has commenced. On the other hand, the rinse water tank 102 and the process water tank 14 are drained to low level prior to commencing the cleaning cycle.

Output solution from the storage tank 76 is routed via a valve 126 to fill the process water tank 14 via a spray bar 128. The spray bar 128 causes the output solution to be sprayed onto the tank walls throughout the filling process. Once process water tank 14 is full to the predetermined level, the output solution is pumped by pump 44 through the cell pack into the weir tank 70. The output solution is then drained to waste via the valve 76.

When the "cleaning" output solution reaches a low level in the process water tank 14 as detected by the level detector 26, the tank 14 is re-filled with output solution via the valve 126. Output solution is then pumped by the pump 44 from the process water tank 14 and the valve 46 is opened to divert the output solution to the rinse water tank 102 via a spray bar 130. When the rinse water tank 102 is filled, the tank is held full for about five minutes in anticipation of a demand to flush the rinse water line. If no signal is received, the rinse water tank 102 is allowed to drain along with the process water tank 14 and the storage tank 76.

Figure 3:
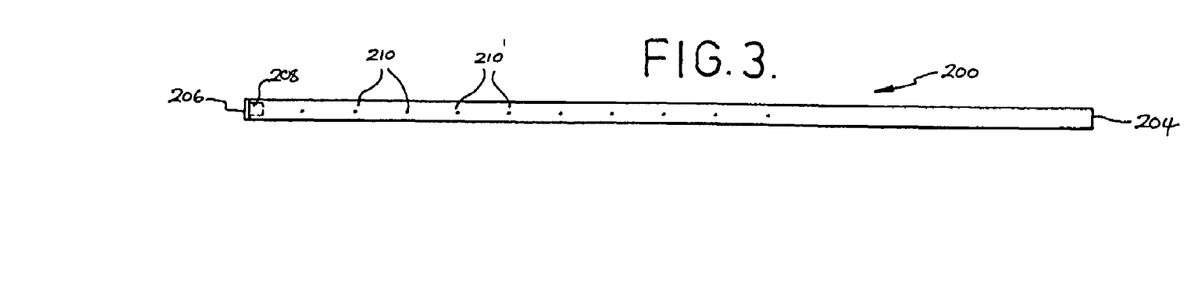
FIG. 3 illustrates a dispenser in accordance with another aspect of the invention.

FIG. 3 shows a dispenser 200 for uniformly dispersing two miscible liquids. The dispenser 200 is in the form of an elongate tube 202 having an open first end 204 and a second end 206 closed by an end cap 208. The tube 202 is provided with a row of perforations 210 substantially along its length. In use in the method of the invention, the open first end 204 of the dispenser 200 is fixed to the end of the feed line for the concentrated salt solution which is pulse fed from the make up tank 20 (FIG. 2) by the peristaltic pump 48. The dispenser 200 is located in and aligned with the flow path of process water which is continuously pumped from the process water tank 14 by the pump 44. As the pulses of concentrated salt solution arrive in the dispenser 200, the solution is forced out through the perforations 210 into the process water flow. The resulting saline solution is of substantially homogeneous concentration by virtue of the mixing pattern achieved by the dispenser 200.

The dilution of the saturated salt solution is determined by the length of the dispenser 200, or rather the length over which the perforations are provided, the pulse rate of the saturated salt solution and the velocity of the process water.

Figure 4:
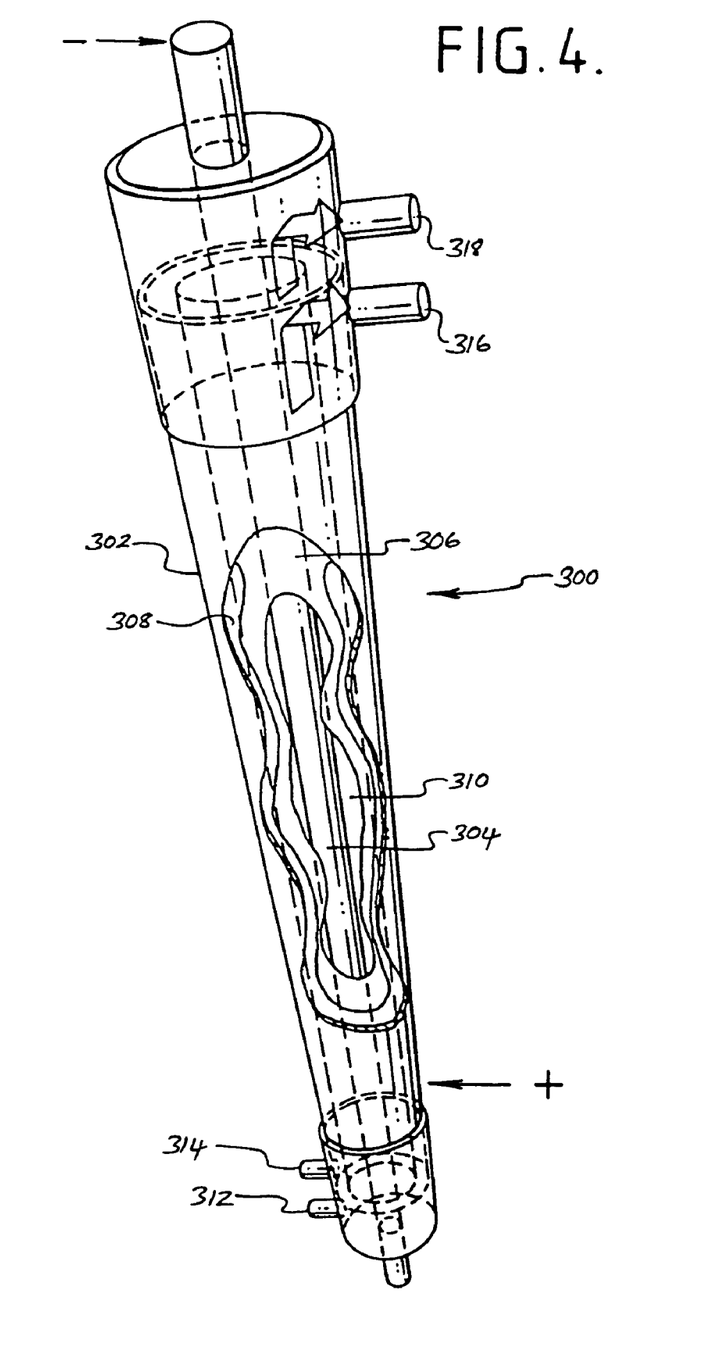
FIG. 4 shows an electrolytic cell for use in the present invention.

FIG. 4 shows an electrolytic cell 300 as used in the present invention. The cell 300 comprises co-axial cylindrical and rod electrodes 302, 304 respectively, separated by a semi-permeable ceramic membrane 306 co-axially mounted between the electrodes thus splitting the space between the electrodes to form two chambers 308, 310. The cylindrical electrode 302 forming the anode is typically made from commercially pure titanium coated with an electrocatalytic (active) coating suitable for the evolution of chlorine from a chloride solution. The rod electrode 304 forming the cathode is made from titanium and machined from an 8 mm stock bar to a uniform cross-section over its effective length, which is typically about 210 mm±0.5 mm. The semi-permeable ceramic membrane 306 forming a separator and creating the anode and cathode chambers 308 and 310 is composed of aluminium oxide (80%), zirconium oxide (18.5%) and yttrium oxide (1.5%), and has a porosity of about 50-70%, a pore size of 0.3 to 0.5 microns and a wall thickness of 0.5 mm+0.3 mm/−0.1 mm. The ceramic of the membrane 306 is more fully disclosed in the specification of patent application number GB 9914396.8, the subject matter of which is incorporated herein by reference.

The cell 300 is provided with entry passages 312, 314 to permit the saline solution to enter the cell 300 and flow upwards through the anode and cathode chambers 308 and 310 and is discharged as anolyte and catholyte through exit passages 316, 318 respectively. The anolyte containing available free chlorine constitutes the output solution.

As previously described, in order to provide a useful amount of output solution within a reasonable period of time, a group of cells are connected together to form a cell pack. For example, a cell pack comprising eight cells connected together in parallel hydraulically and in series electrically is capable of generating about 200 liters/hour of output solution.

Although the invention has been particularly described, it should be appreciated that the invention is not limited to the particular embodiments described and illustrated, but includes all modifications and variations falling within the scope of the invention as defined in the appended claims. For example, means other than the elongate, perforated dispenser described for mixing the concentrated salt solution with process water to produce a homogeneous saline solution may be used. Indeed, the concentrated salt solution can be continuously fed into a stream of process water rather than being pulse fed. In addition, while a weir tank is described as being particularly suitable for providing intermediate holding means for the output solution, other types of holding means may be used, such as a more conventional tank having appropriate outlet means for transferring its contents to the output solution storage tank. The cell separator can be made of ceramics other than the aluminium oxide, zirconium oxide and yttrium oxide ceramic described and of any other suitable semi-permeable or ion-selective material.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. Apparatus for producing an output solution having a predetermined level of available free chlorine comprising: an electrolytic cell, means for passing a saline solution having a substantially constant chloride ion concentration through the electrolytic cell to produce a substantially constant chloride ion throughput, means for applying a substantially constant current across the cell, and means for dispensing the output solution having the predetermined level of available free chlorine from the electrolytic cell.

2. Apparatus according to claim 1, wherein the electrolytic cell comprises anode and cathode chambers separated by a separator, each chamber having a feed line through which the saline solution is fed into the chamber and anolyte and catholyte lines respectively for receiving the electrochemically treated solution.

3. Apparatus according to claim 2, wherein the output solution comprises the anolyte.

4. Apparatus according to claim 3, further comprising a catholyte recirculation line for feeding at least a portion of catholyte from the cathode chamber to the input line of the anode chamber.

5. Apparatus according to claim 1, further comprising a concentrated salt solution make up tank, a process water tank and mixing means for mixing a concentrated salt solution from the make up tank with process water from the water tank to produce the saline solution.

6. Apparatus according to claim 5, wherein the mixing means comprises a dispenser for dispersing pulses of concentrated salt solution into a continuous flow of process water.

7. Apparatus according to claim 6, wherein the dispenser comprises a tube having a closed end, an open, feed end and a plurality of apertures along its length.

8. Apparatus according to claim 5, wherein the electrolytic cell is positioned at a level higher than the concentrated salt solution make up tank and the process water tank thereby to reduce back pressure on the cell.

9. Apparatus according to claim 1, further comprising an intermediate holding tank for receiving output solution from the cell.

10. Apparatus according to claim 9, further comprising measuring means to measure biocidal efficacy of the output solution in the intermediate holding tank.

11. Apparatus according to claim 10, wherein the measuring means comprises a pH meter and a redox probe.

12. Apparatus according to claim 9, further comprising a storage tank for receiving output solution from the intermediate holding tank.

13. Apparatus according to claim 12 wherein the intermediate holding tank comprises a weir tank located above the storage tank.

14. Apparatus according to claim 13, wherein the storage tank is positioned at a height to allow output solution to be dispensed therefrom by gravity feed.

15. Apparatus according to claim 9, further comprising a rinse water storage tank for receiving output solution from the intermediate holding tank and water.

16. Apparatus according to claims 15, wherein the rinse water storage tank is positioned at a height to allow rinse water comprising output solution diluted with water to be dispensed therefrom by gravity feed.

17. Apparatus according to claim 9, further comprising corrosion inhibitor storage and dispensing means for dosing corrosion inhibitor into the intermediate holding tank.

18. Apparatus according to claim 1, further comprising a user interface for displaying information on the performance of the apparatus and the materials inputted to and outputted from the apparatus.

19. Apparatus according to claim 18, wherein the user interface includes a display with keypad controls.

20. Apparatus according to claim 18, further comprising control means to permit adjustment of operating parameters in response to information displayed.

21. Apparatus according to claim 1, further comprising a service interface for displaying diagnostic information on the performance of the apparatus.

22. Apparatus according to claim 21, wherein the service interface includes means to permit adjustment of operating parameters.

23. Apparatus according to claim 21, wherein the service interface can be accessed remotely.

24. Apparatus according to claim 1, further including one or more failsafe mechanisms to prevent output solution from being dispensed when operating parameters cannot be adjusted to ensure that the solution has the required biocidal properties or when the output solution is older than a predetermined age.

25. An apparatus for producing an output solution having a predetermined level of available free chlorine comprising:
an electrolytic cell having an inlet for receiving an input solution and an outlet for expelling the output solution,
a concentrated salt solution tank for holding a concentrated salt solution having chloride ions,
a water tank for holding water, connected to a water pump,
means for diluting the concentrated salt solution with the water to form the input solution prior to the electrolytic cell inlet,
a conductivity sensor located prior to the inlet of the electrolytic cell for measuring the conductivity of the input solution, and
means for adjusting the flow of chloride ions into the input solution to maintain a constant chloride ion throughput through the electrolytic cell.

* * * * *